US011022663B2

(12) United States Patent
Carlsson et al.

(10) Patent No.: US 11,022,663 B2
(45) Date of Patent: Jun. 1, 2021

(54) COMMUNICATION CHANNEL

(71) Applicant: ELEKTA LTD., Crawley (GB)

(72) Inventors: Per Carlsson, Täby (SE); Erik Carlander, Stockholm (SE); Henrik Alexis, Vaxholm (SE); Maja Nilsson, Johanneshov (SE)

(73) Assignee: ELEKTA LTD., Crawley (GB)

( * ) Notice: Subject to any disclaimer, the term of this patent is extended or adjusted under 35 U.S.C. 154(b) by 749 days.

(21) Appl. No.: 15/585,662

(22) Filed: May 3, 2017

(65) Prior Publication Data
US 2018/0321336 A1  Nov. 8, 2018

(51) Int. Cl.
*G01R 33/28* (2006.01)
*A61N 5/10* (2006.01)
*A61B 6/04* (2006.01)
*A61B 5/055* (2006.01)
*A61G 13/10* (2006.01)
*A61G 13/00* (2006.01)

(52) U.S. Cl.
CPC ............ *G01R 33/283* (2013.01); *A61B 5/055* (2013.01); *A61B 6/0407* (2013.01); *A61G 13/104* (2013.01); *A61N 5/10* (2013.01); *A61N 5/1077* (2013.01); *A61B 6/0471* (2013.01); *A61G 13/0018* (2013.01); *A61G 2210/50* (2013.01); *A61N 2005/1097* (2013.01)

(58) Field of Classification Search
CPC ....... A61B 6/04; A61B 6/0407; A61B 6/0442; A61B 6/0457; A61B 5/0555

USPC .... 5/601, 600, 904, 905, 943; 378/209, 208, 378/20
See application file for complete search history.

(56) References Cited

U.S. PATENT DOCUMENTS

| 4,131,802 | A | * | 12/1978 | Braden | A61B 6/0442 250/363.02 |
| 4,583,242 | A | * | 4/1986 | Vinegar | G01N 33/24 378/20 |
| 4,641,823 | A | * | 2/1987 | Bergman | A61B 5/0555 5/81.1 HS |
| 5,197,474 | A | * | 3/1993 | Englund | A61B 5/0555 324/318 |
| 5,494,051 | A | * | 2/1996 | Schneider, Sr. | A61G 1/00 128/870 |
| 5,749,374 | A | * | 5/1998 | Schneider, Sr. | A61G 1/00 128/870 |

(Continued)

FOREIGN PATENT DOCUMENTS

| CN | 1489975 A | 4/2004 |
| EP | 2881033 A1 | 6/2015 |

(Continued)

*Primary Examiner* — Robert G Santos
(74) *Attorney, Agent, or Firm* — Birch, Stewart, Kolasch & Birch, LLP

(57) ABSTRACT

A system for moving a patient into and from a medical apparatus includes a patient support arranged outside a treatment space of a medical apparatus, a treatment table arranged inside the treatment space in the medical apparatus and a patient bed movable in a longitudinal direction from the patient support to the treatment table and back by means of activation of a transferring mechanism. The patient bed is provided with at least a first communication channel for transferring communication signals.

16 Claims, 3 Drawing Sheets

(56) References Cited

U.S. PATENT DOCUMENTS

| | | | | |
|---|---|---|---|---|
| 5,808,468 A * | 9/1998 | Bis | ............... | A61B 5/0555 |
| | | | | 324/318 |
| 6,493,571 B1 * | 12/2002 | Bis | ............... | A61B 5/0555 |
| | | | | 324/307 |
| 6,668,403 B2 * | 12/2003 | Seufert | ............ | A61B 6/0471 |
| | | | | 378/209 |
| 7,810,194 B2 * | 10/2010 | Clenet | ............ | A47C 21/003 |
| | | | | 5/659 |
| 9,901,501 B2 * | 2/2018 | Lewald | ............ | A61G 7/103 |
| 10,864,130 B2 * | 12/2020 | Lewald | ............ | A61G 7/103 |
| 2002/0112288 A1 * | 8/2002 | Seufert | ............ | A61B 6/0471 |
| | | | | 5/601 |
| 2004/0064028 A1 | 4/2004 | Deimling | | |
| 2008/0263775 A1 * | 10/2008 | Clenet | ............ | A47C 21/003 |
| | | | | 5/694 |
| 2015/0150740 A1 * | 6/2015 | Lewald | ............ | A61G 7/103 |
| | | | | 600/415 |
| 2018/0133080 A1 * | 5/2018 | Lewald | ............ | A61G 7/103 |
| 2018/0321336 A1 * | 11/2018 | Carlsson | ............ | A61B 6/0407 |

FOREIGN PATENT DOCUMENTS

| | | | | |
|---|---|---|---|---|
| EP | 3398653 A1 * | 11/2018 | ............ | A61B 5/0555 |
| EP | 3398653 B1 * | 11/2019 | ............ | A61G 13/104 |
| JP | 2014-200609 A | 10/2014 | | |
| WO | WO 2016/090384 A2 | 6/2016 | | |

* cited by examiner

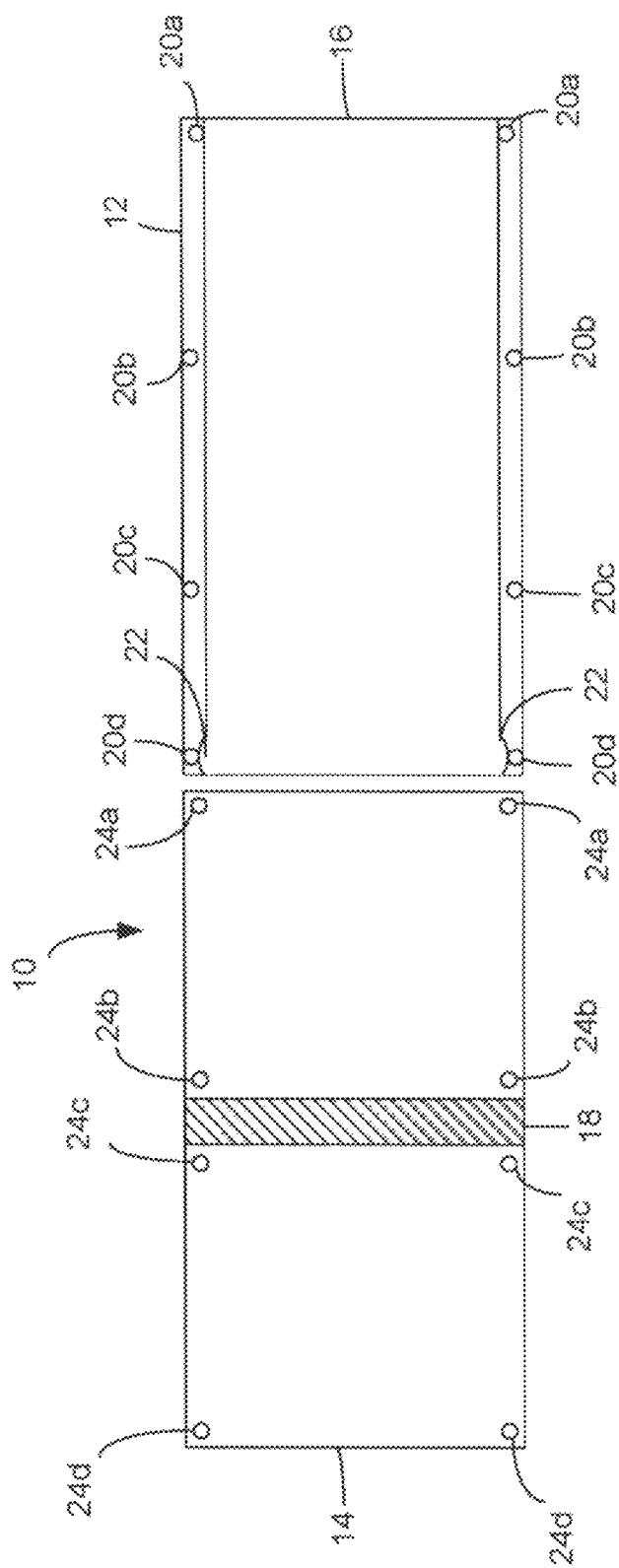
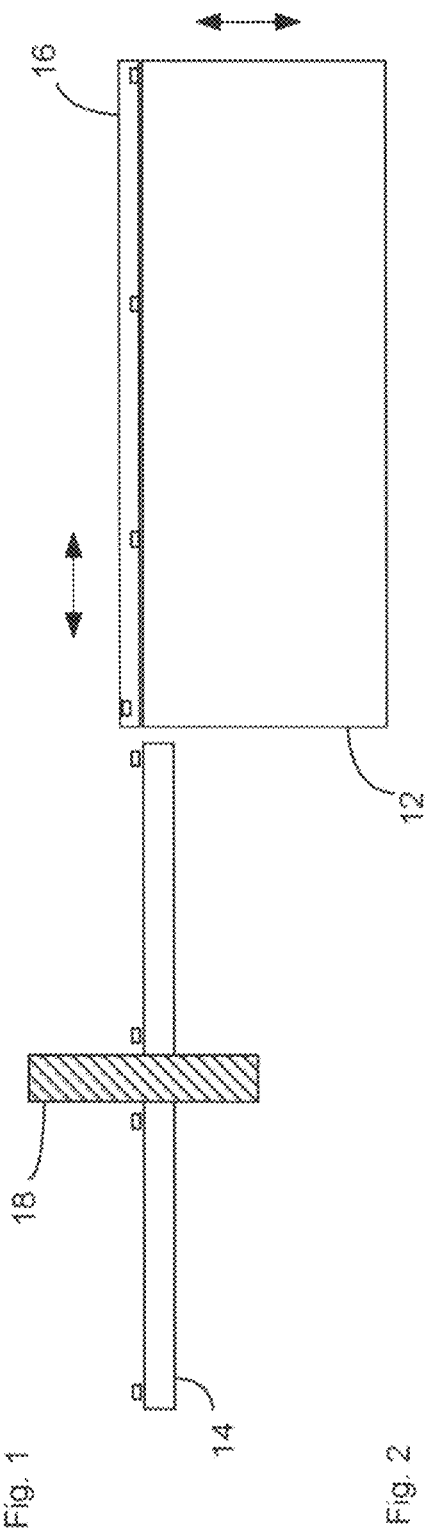
Fig. 1
Fig. 2

COMMUNICATION CHANNEL

TECHNICAL FIELD

The present invention relates to medical devices, and particularly to systems and devices for moving a patient to and from a radiotherapy system. The invention further refers to a system for communication between medical personnel and patient.

BACKGROUND

In radiotherapy systems, such as MR Linac systems, the alignment of the patient is critical as the area of the patient being treated or imaged should be aligned as centrally as possible with respect to the treatment radiation plane and as reproducible as possible. One source of potential inaccuracy in the alignment is the repositioning of the bed on which the patient rests. As many medical radiotherapy systems require the patient to be placed into an enclosed and confined space, hereinafter called treatment bore, the patient must be set up for treatment outside the treatment bore and then transported into the treatment bore for the medical treatment to begin. Therefore, the bed must be movable between these two locations and positionable to a high degree of accuracy as misalignment during set up may entail that the patient will need to be removed from the medical radiotherapy system and realigned before treatment can commence, and thus wasting time and resources.

It is also of very high importance that the patient positioning is as stable as possible during the movement as well during the treatment or imaging. Hence, the position of the bed in treatment bore in the medical radiotherapy system must be very stable. The process of moving the bed from its support outside the medical radiotherapy system into the treatment bore inside the medical radiotherapy system itself requires careful alignment with the treatment table of the system as well as a high degree of stability.

Furthermore, it is also important that the process patient set up and of moving the bed from its support outside the medical radiotherapy system into the treatment space inside the medical radiotherapy system is secure for the patient and easy to handle for the medical staff. The risk of patient injuries must be minimized during movement as well as during treatment in order to provide as high patient security as possible and minimize risk for patient movements during treatment.

Moreover, the medical radiotherapy system, in particular in MR Linac systems, it is of very high importance that all material in the treatment bore or treatment volume is known and taken into account in the planning system. As all material will absorb radiation dose, it is important to reduce the material present in the treatment bore as much as possible and it is also important that the positions of material structures are known.

Since the treatment bore can perceived as a claustrophobic space and also since the patient to be treated may be injured or sick, communication between medical personnel and the patient should be provided to avoid a panic situation of the patient. Since cables and the like from the patient (head) to medical personnel are not suitable as they can influence magnetic resonance imaging or the dose of radiation during treatment, other solutions are required to ensure communication between patient and medical personnel. Cables and other round communication lines absorb an unknown amount of radiation and/or magnetism and may thus make it difficult to predict the radiation dose administered to the patient and target volume, respectively. Additionally the absorption of magnetism may lead to bad image quality. Further, Bluetooth and other wireless communication does not work to and from the treatment volume due to the magnetic field in the treatment volume thus a communication using these technologies is not possible once the patient is positioned in the treatment volume.

There is however a need to provide communication between the patient and the medical staff, in particular when the patient is positioned in the treatment volume.

SUMMARY OF THE INVENTION

An object of the present invention is to provide a user and patient friendly movable bed and treatment table for use in medical radiotherapy systems, such as MR Linac systems.

Another object is to provide a reliable communication between the patient and the medical staff when the patient is positioned in the treatment volume.

This and other objects are fulfilled by the present invention as defined by the independent claims. Preferred embodiments are defined by the dependent claims.

Disclosed herein is a system for moving a patient into and from a medical apparatus, comprising a patient support arranged outside a treatment space of a medical apparatus, a treatment table arranged inside the treatment space in the medical apparatus, a patient bed movable in a longitudinal direction from the patient support to the treatment table and back by means of activation of a transferring mechanism. The patient bed is provided with at least a first communication channel for transferring communication signals.

Such a communication channel may allow the communication between patient and medical staff even when the patient is positioned in the treatment volume.

In an embodiment the first communication channel runs in a substantially longitudinal direction of said bed. The first communication channel may in particular run along the entire length of the patient bed, for example underneath it or on the lateral side of the patient bed.

In an embodiment the first communication channel is air-filled.

In another embodiment the first communication channel runs from a first end of said bed to a second end of said bed.

In a further embodiment at least one first connection device is arranged at said first end for connecting an external device to said communication channel.

In another embodiment at least one second connection device is arranged at said second end for connecting an external device to said communication channel.

The first connection device and the second connection device may comprise interfaces or terminals for microphones and loudspeakers or earphones. The microphone, in particular if it sits at the patient head end, thus the first end, may be a neck-microphone or a throat microphone. A neck-microphone or even a throat microphone may reduce the distance between first connection device and microphone and thus reduce the amount of electronic material, cables and further material in the treatment volume that is affecting the radiation dose and or the quality of the images of the magnetic resonance imaging system. Neck- or throat microphones are both contact microphones.

Additionally, depending on the position of the target volume or tissue in the patient, a pipe may be positioned close to the patient's head without disturbing the radiation dose but still close enough for the patient to hear sound coming from the pipe. The pipe is preferably coupled to one of the communication channels in order to let sound travel through the communication channel from the operator to the patient. In order to allow the patient to hear the sound the pipe end not coupled to the communication channel may be open in order to let the sound reach the patient's ear. This may for example be the case if the target volume or tissue is close to the patient's ear, for example a tumor located very close to the ear. If the target volume is not located close to the ear, earphones may be used to provide audio/sound to the patient.

The first communication channel may have a circular cross section.

The circular cross section may improve the travelling of waves and reduce losses in the first communication channel.

In a further embodiment the patient bed comprises at least two, a first and a second, communication channels.

In an embodiment the second of the two communication channels is used to deliver signals from the first end to the second end and the first of the at least two communication channels to deliver signals from the second end to the first end.

In other words, the first communication channel can be used to provide communication from outside the treatment volume into the treatment volume. The second communication channel can be used to provide communication from the treatment volume to the outside of the treatment volume. Thus one, for example the first communication channel provides the patient with information while the other, for example the second communication channel provides an operator with information from the patient.

The first communication channel can be connected to the pipe having an open end for providing the sound to the patient in the treatment volume.

The signals may be light or sound signals.

Separating the ingoing and outgoing signals may avoid any disturbances.

As previously indicated the external devices may comprise a microphone and/or a loudspeaker to receive and/or send sound through the communication channel.

The first and second communication channels may further comprise an emitting device at the first and second end, respectively, and a receiving device at the second and first end, respectively.

The receiving and emitting devices, respectively may be configured to emit and/or receive sound/audio.

In an alternative embodiment the emitting device and receiving device, respectively, may be configured to emit and/or receive light signals. Such light signals may be translated into audio or sound for example by a computer or computer circuitry located at the first and second end, respectively. Such computers or computer circuitry may be directly connected to the emitting and receiving devices.

The communication channels are integrated parts of the table and the channels are sealed at the connections to external devices, parts or units using, for example, by plate and epoxy.

The microphones and loudspeakers may further be connected to printed circuit boards, computers or other processors and memory for conversion, amplification and/or filtering.

BRIEF DESCRIPTION OF THE DRAWINGS

For a better understanding of the present invention, and to show more clearly how it may be carried into effect, reference will now be made, by way of example, to the following drawings, in which:

FIG. 1 shows a plan view of a system according to embodiments of the present invention;

FIG. 2 shows a side view of the system according to embodiments of the present invention;

DESCRIPTION

Figure 3:
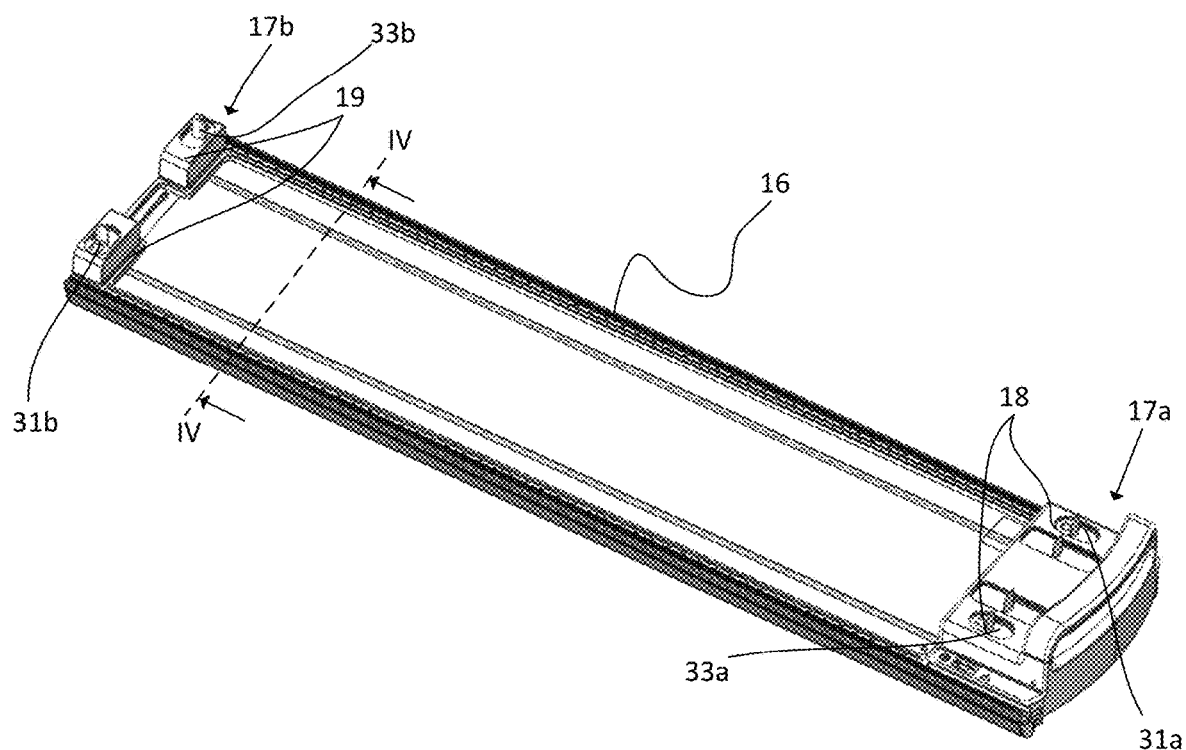
FIG. 3 shows a perspective view of a patient bed according to embodiments of the present invention.

FIG. 1 shows a plan view of a system 10 according to embodiments of the present invention and FIG. 2 shows a side view of the system of FIG. 1. The system 10 comprises a patient support 12, a treatment table 14, and a bed 16 which is movable between the patient support 12 and the treatment table 14. The treatment table 14 is schematically shown in FIGS. 1 and 2 and may form part of any medical treatment system but is particularly suitable for use in MR Linac radiotherapy systems. Hence, in embodiments of the present invention, the system 10 is arranged at a MR Linac radiotherapy system having radiation heads and radiation sources for generating beams of therapeutic radiation emanating from the radiation heads. One or more collimating elements (e.g. a Multi-leaf collimator in the Linac part) are provided for shaping the beam to conform to a desired cross-section. The radiation heads may be mounted on a rotatable gantry, and controlled to rotate around the patient while directing the radiation towards the axis of rotation and the target within the patient. The target thus receives radiation from multiple angles and a higher dose than the surrounding healthy tissue. The extent of the treatment area 18, i.e. the volume in which the radiation beam operates, is illustrated schematically in FIGS. 1 and 2.

The patient support 12 may comprise a mechanism for altering the height of the support, for example, between a first height and second height. For example, the first (lower) height may be at a level suitable to allow the patient to climb on to the bed 16, while the second (higher) height is a level equal to the height of the treatment table 14 and allows the bed 16 to move between the support 12 and the treatment table 14.

The bed 16 may be moved in a direction along its longitudinal axis between the support 12 and the treatment table 14 in a manner to be described in more detail below. Those skilled in the art will appreciate that any suitable mechanism may be used for moving the bed 16. For example, the bed 16 may be moved by a pulley/belt system, a rack and pinion system, a conveyor belt, etc.

As described above, it is important that the bed can be smoothly transferred or moved between the support 12 and the treatment table 14 so that once on the table 14 the bed is correctly aligned within the system, which in many radiotherapy systems is crucial. In order to ensure that the bed 16 is correctly aligned during initial set-up and treatment, the system 10 may comprise guide elements 20a, 20b, 20c, 20d, arranged on an upper surface of the support 12. Alternatively, guide tracks may be arranged on an upper surface of the support 12 and treatment table 14 and corresponding guide rails may be arranged on the patient bed 16 such that the bed 16 can slide seamlessly between the support and the table.

In the illustrated embodiment, the patient support comprises four pairs of guide elements. However, fewer or more guide pairs may be provided without departing from the scope of the invention. The guide pairs may be uniformly spaced, along the edges of the support 12 so as to prevent the bed 16 from moving significantly in the lateral direction (i.e. up and down the page in FIG. 1, or into and out of the page in FIG. 2).

In the embodiment illustrated in FIGS. 1 and 2, the guide elements are rollers which move over the edge of the bed 16 as the bed moved in the direction along its longitudinal axis. However, those skilled in the art will appreciate that any suitable guiding element which provides a low friction surface along which the bed can travel without sticking may be provided as an alternative. Further, guides needs not be identical, and a mix of different guides may be provided in the same system without departing from the scope of the invention.

The treatment table 14 may comprise a plurality of guide elements 24a, 24b, 24c, 24d, on an upper surface of the table, similar to the guide elements on the support 12.

Figure 4:
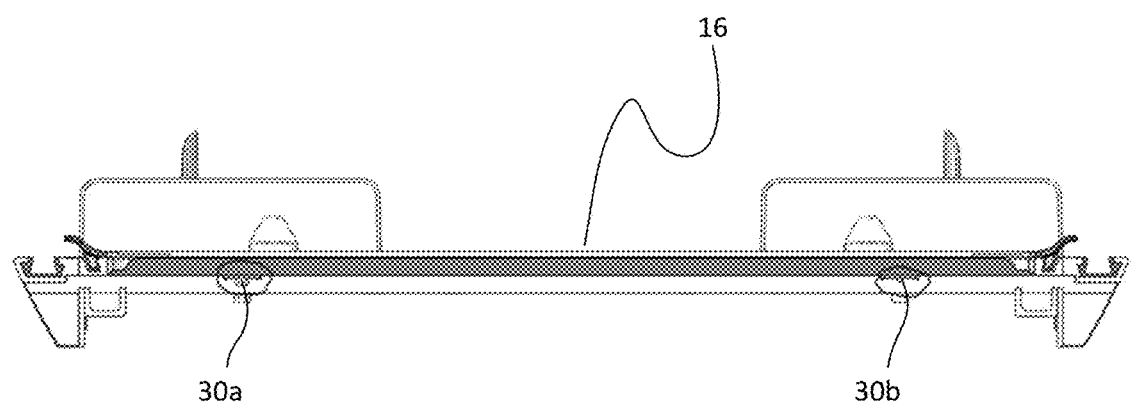
FIG. 4 shows a cross section through the patient bed of FIG. 3 at line VI-VI.

FIG. 3 illustrates a perspective view of a patient bed 16. The patient bed 16 has a generally rectangular shape and a first end 17a and a second end 17b. The first end 17a comprises a first connection device 18 and the second end 17b a second connection device 19. The first and second connection device 18, 19 may each comprise terminals for connecting for example a microphone through a first terminal 31a, 31b and a loudspeaker or earphones through a second terminal 33a, 33b. The positions of the first and second terminals 31a, 31b, 33a, 33b are exchanged at the first end 17a relative to the second end 17b. The microphone connected to the patient, thus the first end 17a, will be connected via the first terminal 31a, a second communication channel 30b (c.f. FIG. 4) and the second terminal 33b to a loudspeaker or earphones on the medical staff side, thus the second end 17b. The microphone of the medical staff will be connected to the first terminal 31b on the second end 17b, while the first terminal 31b on the second end 17b is connected, via a first communication channel 30a (c.f. FIG. 4) to the first terminal 33a on the first end 17a. The first terminal 31a on the first end 17a is a signal input terminal, the second terminal 33b on the second end 17b a signal output terminal, the first terminal 31b on the second end 17b is a signal input terminal and the second terminal 33a a signal output terminal.

The patient bed 16 comprises at least two, a first and a second communication channel 30a, 30b as illustrated in FIG. 4. FIG. 4 illustrates a cross section cut through the patient bed 16 of FIG. 3 at illustrated line IV-IV and as seen in the direction of the arrows. The communication channels 30a, 30b are arranged on an under side of the patient bed 16 as shown in FIG. 4. At the first end 17a and the second end 17b the communication channels 30, 30' may be connected to the first and second connection devices 18, 19 and first and second terminals 31a, 31b, 33a, 33b, respectively. The first communication channel 30a is connected to the second terminal 33a on the first side 17a and the first terminal 31b on the second side 17b. The second communication channel 30b is connected to the first terminal 31a on the first side 17a and the second terminal 33b on the second side 17b. The first and second communication channels 30a, 30b are designed to provide a channel for signals to travel in. The first communication channel 30a is thereby used to let a signal travel from the second end 17b to the first end 17a and the second communication channel 30b is used to let a signal travel from the first end 17a to the second end 17b. The traveling direction of the signal in the first and second communication channels may be exchanged.

Each of the first and second communication channels 30a, 30b comprise an emitting device (not shown) on one of the first and second end 17a, 17b and a receiving device (not shown) on the other of the first and second end 17a, 17b. These emitting and receiving devices may be connected to the corresponding first and second terminals 31a, 31b, 33a, 33b via circuit boards or computer circuits. Such computer circuits may even allow to change the direction of signal traveling in the first or second communication channel 30a, 30b, thus one communication channel may be enough to ensure communication between medical staff and patient during treatment.

The communication channels 30a, 30b may extend through a recess in the patient bed 16 at the first end 17a and the second end 17b, respectively.

Figure 5:
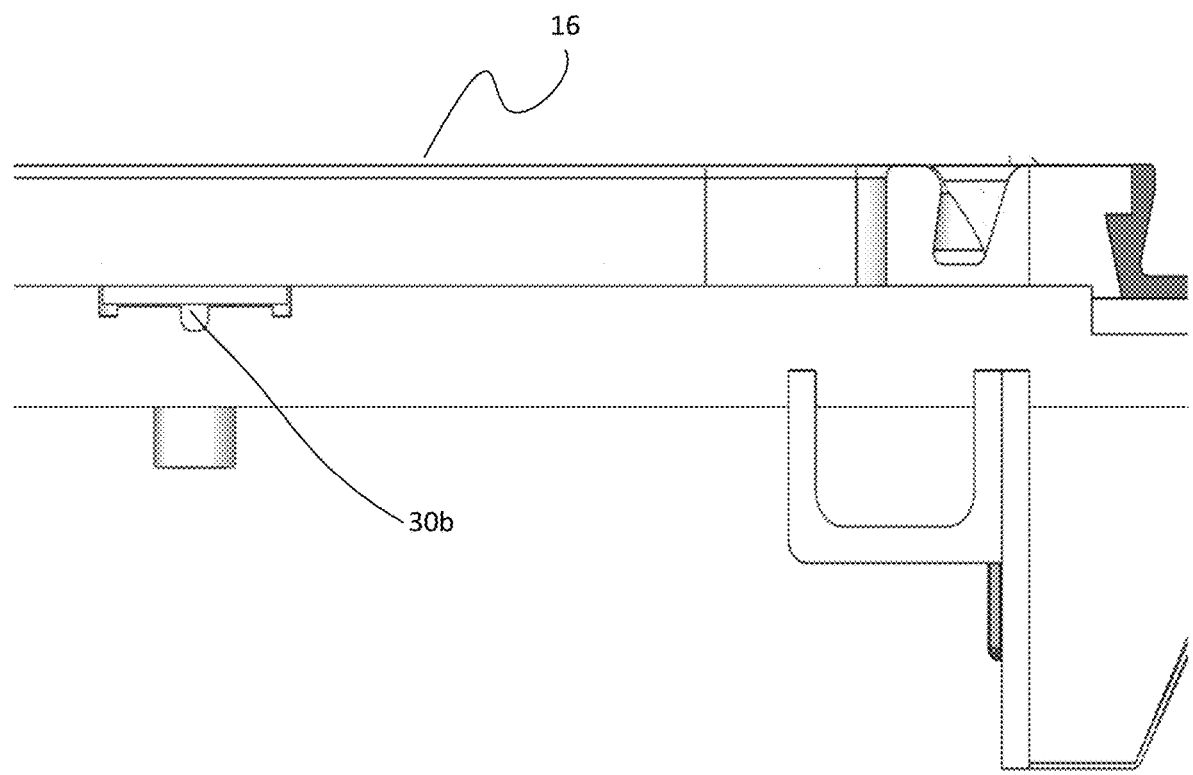
FIG. 5 shows an enlarged part of FIG. 4.

FIG. 5 illustrates an enlarged view of FIG. 4 obscuring certain parts shown in FIG. 4 and illustrating the second communication channel 30b. The second communication channel 30b is illustrated and so is the patient bed 16. In FIGS. 4 and 5 the communication channels 30a, 30b have been illustrated as having a circular or at least partially circular cross section. The cross sectional shape may however have another shape, such as completely circular, rectangular, a polygon shape etc. This may depend on acoustic requirements.

The invention has now been described referring to FIGS. 1 to 5. As previously mentioned a part of the invention may be to use a neck-microphone or a throat microphone on the patient in order to reduce cable length and electronic components in the treatment volume. A neck microphone is typically connected on an outer side of a person's neck and reads the vibrations when the person speaks using the contact. The same with a throat microphone, with the difference that such a throat microphone is positioned on a person's larynx outside the throat. Additionally small loudspeakers may be used instead of earphones to communicate with the patient, depending on the position of the target volume. Earphones may however still be used if the target volume is not located close to the patient's ears. Further, as previously mentioned, the loudspeaker may be in the form of an open pipe end, not comprising any further electronic equipment, but provided in order to provide sound or audio to the patient from an outer side of the treatment volume using one of the communication channels. The pipe end or the entire pipe may be arranged flexible so that the free and open pipe end can be positioned close to the patient's ear once the patient is set up on the patient bed. This can ensure that the audio or sound reaches the patient's ear.

The invention claimed is:

1. A system for moving a patient into and from a medical apparatus, comprising:
    a patient support arranged outside a treatment space of a medical apparatus;
    a treatment table arranged inside the treatment space in the medical apparatus; and
    a patient bed movable in a longitudinal direction from the patient support to the treatment table and back by means of activation of a transferring mechanism, the patient bed including a first end and a second end,
    wherein the patient bed is provided with at least two communication channels, including a first communication channel and a second communication channel, for transferring communication signals, and
    wherein the second communication channel is used to deliver signals from the first end of the patient bed to the second end of the patient bed, and the first communication channel is used to deliver signals from the second end of the patient bed to the first end of the patient bed.

2. The system according to claim 1, wherein said first communication channel runs in a substantially longitudinal direction of said bed.

3. The system according to claim 2, wherein said first communication channel is air-filled.

4. The system according to claim 1, wherein said first communication channel is air-filled.

5. The system according to claim 1, wherein at least one connection device is arranged at said first end of the patient bed for connecting an external device to said first communication channel.

6. The system according to claim 5, wherein the external device is a microphone or a loudspeaker.

7. The system according to claim 1, wherein at least one connection device is arranged at said second end of the patient bed for connecting an external device to said first communication channel.

8. The system according to claim 7, wherein the external device is a microphone or a loudspeaker.

9. The system according to claim 1, wherein said first communication channel may have a circular cross section, an at least partially circular cross section, a rectangular cross-section, or a polygon shaped cross-section.

10. The system according to claim 1, wherein said first communication channel comprises an emitting device at one of the first and second ends and a receiving device at the other of the first and second ends.

11. The system according to claim 10, wherein the receiving and emitting devices are sound emitting and receiving devices.

12. The system according to claim 11, wherein the sound receiving and emitting devices comprise a computer or computer circuitry for improving, amplifying and/or filtering the sent or received sound.

13. The system according to claim 10, wherein the receiving and emitting devices are light emitting and receiving devices.

14. The system according to claim 13, wherein the light receiving and emitting devices comprise a computer or computer circuitry for translating light signals into sound and sound into light signals, respectively.

15. The system according to claim 1, wherein the system is configured to be used in an MR Linac apparatus.

16. A system for moving a patient into and from a medical apparatus, comprising:
   a patient support arranged outside a treatment space of a medical apparatus;
   a treatment table arranged inside the treatment space in the medical apparatus; and
   a patient bed movable in a longitudinal direction from the patient support to the treatment table and back by means of activation of a transferring mechanism, the patient bed including a first end and a second end,
   wherein the patient bed is provided with at least a first communication channel for transferring communication signals,
   wherein said first communication channel is air-filled,
   wherein the patient bed further comprises a second communication channel, and
   wherein the second communication channel is configured to deliver signals from the first end of the patient bed to the second end of the patient bed, and the first communication channel is configured to deliver signals from the second end of the patient bed to the first end of the patient bed.

* * * * *